(12) United States Patent
Young et al.

(10) Patent No.: US 10,869,945 B2
(45) Date of Patent: Dec. 22, 2020

(54) DIFFUSER WITH INTERCHANGEABLE COVER

(71) Applicant: Young Living Essential Oils, LC, Lehi, UT (US)

(72) Inventors: D. Gary Young, Alpine, UT (US); Mary Young, Alpine, UT (US); Tyler A. Nanto, Pleasant Grove, UT (US); James T. Davis, II, Springville, UT (US); Brian White, Mapleton, UT (US); William Pipkin, Orem, UT (US)

(73) Assignee: YOUNG LIVING ESSENTIAL OILS, LC, Lehi, UT (US)

( * ) Notice: Subject to any disclaimer, the term of this patent is extended or adjusted under 35 U.S.C. 154(b) by 4 days.

(21) Appl. No.: 14/815,615

(22) Filed: Jul. 31, 2015

(65) Prior Publication Data

US 2016/0243576 A1 Aug. 25, 2016

Related U.S. Application Data

(60) Provisional application No. 62/120,291, filed on Feb. 24, 2015.

(51) Int. Cl.
*B05B 17/06* (2006.01)
*A61L 9/12* (2006.01)
(Continued)

(52) U.S. Cl.
CPC .................. *A61L 9/12* (2013.01); *A61L 9/032* (2013.01); *A61L 9/122* (2013.01); *A61L 9/14* (2013.01);
(Continued)

(58) Field of Classification Search
CPC ........ B05B 17/0646; A61L 9/12; A61L 9/032; A61L 9/122; A61L 9/14; A61L 2209/11; A61L 2209/133; A61L 2209/132
(Continued)

(56) References Cited

U.S. PATENT DOCUMENTS 1,534,624 A    4/1925   Weidlich
4,410,139 A *  10/1983  Nishikawa .......... B05B 17/0615
                                              239/102.2
(Continued)

FOREIGN PATENT DOCUMENTS

EP       0800823 A1    10/1997
WO       2011021980     2/2011

OTHER PUBLICATIONS

U.S. Appl. No. 14/815,615 Office Action Summary dated Mar. 16, 2017.
(Continued)

*Primary Examiner* — Qingzhang Zhou
(74) *Attorney, Agent, or Firm* — Kunzler Bean & Adamson, PC

(57) ABSTRACT

Apparatuses, systems, methods, and computer program products are disclosed for a diffuser and interchangeable cover. A complete diffuser includes a diffuser element that disperses a liquid into air within a diffuser chamber of the complete diffuser. A complete diffuser includes a lid shaped to at least partially enclose an upper opening of a diffuser chamber. A cover is removably couplable to a complete diffuser over a diffuser lid so that a dispersed liquid passes through one or more openings in the cover. A cover includes one or more decorative features having a different external shape than a complete diffuser that receives the cover.

12 Claims, 10 Drawing Sheets

(51) Int. Cl.
*B05B 17/00* (2006.01)
*A61L 9/14* (2006.01)
*A61L 9/03* (2006.01)

(52) U.S. Cl.
CPC ....... *B05B 17/0646* (2013.01); *A61L 2209/11* (2013.01); *A61L 2209/132* (2013.01); *A61L 2209/133* (2013.01)

(58) Field of Classification Search
USPC .................................................. 239/34–60
See application file for complete search history.

(56) References Cited

U.S. PATENT DOCUMENTS

| | | | |
|---|---|---|---|
| 4,640,804 A * | 2/1987 | Mizoguchi | B05B 17/0615 222/108 |
| 5,000,383 A * | 3/1991 | van der Heijden | A01M 1/2044 239/44 |
| D366,722 S | 1/1996 | Yan | |
| 5,487,502 A | 1/1996 | Liao | |
| 5,881,714 A | 3/1999 | Yokoi et al. | |
| 5,908,158 A * | 6/1999 | Cheiman | B05B 17/0615 239/102.2 |
| D416,516 S | 11/1999 | Zee | |
| D448,466 S | 9/2001 | Zaragoza et al. | |
| 6,357,671 B1 | 3/2002 | Cewers | |
| D530,441 S | 10/2006 | Cale et al. | |
| D566,001 S | 4/2008 | Buchenroth, III et al. | |
| 7,441,756 B2 * | 10/2008 | Niedermann | F24F 6/00 261/119.1 |
| D588,687 S | 3/2009 | Drucker et al. | |
| 7,540,432 B2 * | 6/2009 | Majerowski | A01M 1/2044 239/34 |
| D613,844 S | 4/2010 | Jorgensen | |
| D621,494 S | 8/2010 | Lis | |
| D628,281 S | 11/2010 | Bates et al. | |
| 7,837,930 B2 | 11/2010 | Grodsky | |
| D629,330 S | 12/2010 | Dupuis | |
| 7,963,460 B2 | 6/2011 | Jorgensen | |
| 7,992,801 B2 | 8/2011 | Jorgensen | |
| D647,189 S | 10/2011 | Mochizuki et al. | |
| D663,820 S | 7/2012 | Browder | |
| 8,265,466 B2 | 9/2012 | Jorgensen | |
| D685,902 S | 7/2013 | Browder | |
| D693,914 S | 11/2013 | Browder | |
| 8,584,305 B2 | 11/2013 | Won et al. | |
| D706,410 S | 6/2014 | Pan | |
| D720,064 S | 12/2014 | Li | |
| 9,205,165 B2 * | 12/2015 | Gundy | A61L 9/12 |
| D759,798 S | 6/2016 | Young et al. | |
| D766,418 S | 9/2016 | Young et al. | |
| D771,785 S | 11/2016 | Huang | |
| D806,217 S | 12/2017 | Hui | |
| 2005/0185940 A1 | 8/2005 | Joshi et al. | |
| 2006/0222560 A1 | 10/2006 | Stanley, II | |
| 2007/0152081 A1 | 7/2007 | Chou et al. | |
| 2007/0241134 A1 | 10/2007 | Gurrisi et al. | |
| 2008/0027143 A1 * | 1/2008 | Munagavalasa | A01N 53/00 514/724 |
| 2008/0223953 A1 | 9/2008 | Tomono et al. | |
| 2009/0050650 A1 | 2/2009 | Walters et al. | |
| 2010/0308129 A1 * | 12/2010 | Jorgensen | A61L 9/14 239/34 |
| 2011/0024521 A1 * | 2/2011 | Jorgensen | B05B 17/0615 239/102.1 |
| 2011/0248096 A1 | 10/2011 | Lin et al. | |
| 2012/0251296 A1 | 10/2012 | Jorgensen | |
| 2014/0263722 A1 | 9/2014 | Hsiao | |
| 2014/0334801 A1 | 11/2014 | Browder et al. | |
| 2017/0157280 A1 | 6/2017 | Young et al. | |

OTHER PUBLICATIONS

U.S. Appl. No. 15/623,257 Final Office Action dated May 25, 2018.
U.S. Appl. No. 15/623,257 Office Action dated Jan. 11 5, 2018.
U.S. Appl. No. 15/623,257 Office Action dated Oct. 5, 2018.
U.S. Appl. No. 15/439,863 Final Office Action dated May 45, 2018.
U.S. Appl. No. 15/439,863 Office Action dated Oct. 5, 2018.
U.S. Appl. No. 15/439,863 Office Action dated Dec. 29, 2017.
U.S. Appl. No. 29/532,964 Notice of Allowance dated Apr. 25, 2016.
U.S. Appl. No. 29/532,965 Notice of Allowance dated May 9, 2016.
U.S. Appl. No. 29/607,611 Notice of Allowance dated Jun. 15, 2018.
U.S. Appl. No. 15/623,257 Office Action dated May 22, 2019.
U.S. Appl. No. 15/439,863 Final Office Action dated Apr. 19, 2019.
U.S. Appl. No. 15/623,257 Final Office Action dated Oct. 8, 2019.
U.S. Appl. No. 15/439,863 Office Action dated Aug. 9, 2019.
U.S. Appl. No. 15/439,863 Final Office Action dated Mar. 13, 2020, pp. 1-26.

* cited by examiner

DIFFUSER WITH INTERCHANGEABLE COVER

CROSS-REFERENCES TO RELATED APPLICATIONS

This application claims the benefit of U.S. Provisional Patent Application No. 62/120,291 entitled "DIFFUSER TOY" and filed on Feb. 24, 2015 for D. Gary Young, et al., which is incorporated herein by reference.

TECHNICAL FIELD

The present disclosure, in various embodiments, relates to liquid diffusers and more particularly relates to a liquid diffuser with one or more interchangeable covers.

BACKGROUND

Diffusing liquids into the air has a variety of benefits. For example, inhalation of certain liquids may improve a user's respiratory health or may efficiently introduce medication into the bloodstream through the lungs. In another example, liquids can be diffused into the air as a pleasant fragrance or to mask the smell of odorous compounds.

Various devices exist for diffusing liquid into the air. For example, nebulizers, diffusers, and atomizers can deliver liquid particles to the air for inhalation. While such devices may have benefits for children, they are usually designed for adults. These adult focused designs are typically not interactive or educational, and may hold little interest for children.

SUMMARY

Apparatuses are presented for an interchangeable cover for a diffuser. In one embodiment, a removable diffuser cover includes one or more decorative features. A cavity in a diffuser cover, in certain embodiments, is shaped to receive a complete diffuser. In a further embodiment, a complete diffuser comprises a diffuser element that disperses a liquid into air within a diffuser chamber and a lid shaped to at least partially enclose an upper opening of the diffuser chamber. One or more openings in a diffuser cover, in certain embodiments, are positioned to receive a dispersed liquid from a lid of a complete diffuser within a cavity and to allow the dispersed liquid to pass to an exterior of the diffuser cover.

Apparatuses are presented for a diffuser configured to receive an interchangeable cover. In one embodiment, a complete diffuser is shaped to receive a removable cover. A diffuser element of a complete diffuser, in certain embodiments, disperses a liquid into air within a diffuser chamber of the complete diffuser. A lid of a complete diffuser, in a further embodiment, is shaped to at least partially enclose an upper opening of a diffuser chamber and to direct a dispersed liquid through a removable cover in response to the complete diffuser receiving the removable cover.

Systems are presented for a diffuser with an interchangeable cover. In one embodiment, a complete diffuser includes a diffuser element that disperses a liquid into air within a diffuser chamber of the complete diffuser. A complete diffuser, in a further embodiment, includes a lid shaped to at least partially enclose an upper opening of a diffuser chamber. A cover, in one embodiment, is removably couplable to a complete diffuser over a diffuser lid so that a dispersed liquid passes through one or more openings in the cover. A cover, in a further embodiment, includes one or more decorative features having a different external shape than a complete diffuser. In one embodiment, a cover includes one or more openings positioned so that a dispersed liquid passes through the one or more openings and out of the cover. In certain embodiments, a cover includes a controller configured to control one or more operations of a complete diffuser.

BRIEF DESCRIPTION OF THE DRAWINGS

A more particular description is included below with reference to specific embodiments illustrated in the appended drawings. Understanding that these drawings depict only certain embodiments of the disclosure and are not therefore to be considered to be limiting of its scope, the disclosure is described and explained with additional specificity and detail through the use of the accompanying drawings, in which.

DETAILED DESCRIPTION

Figure 1A:
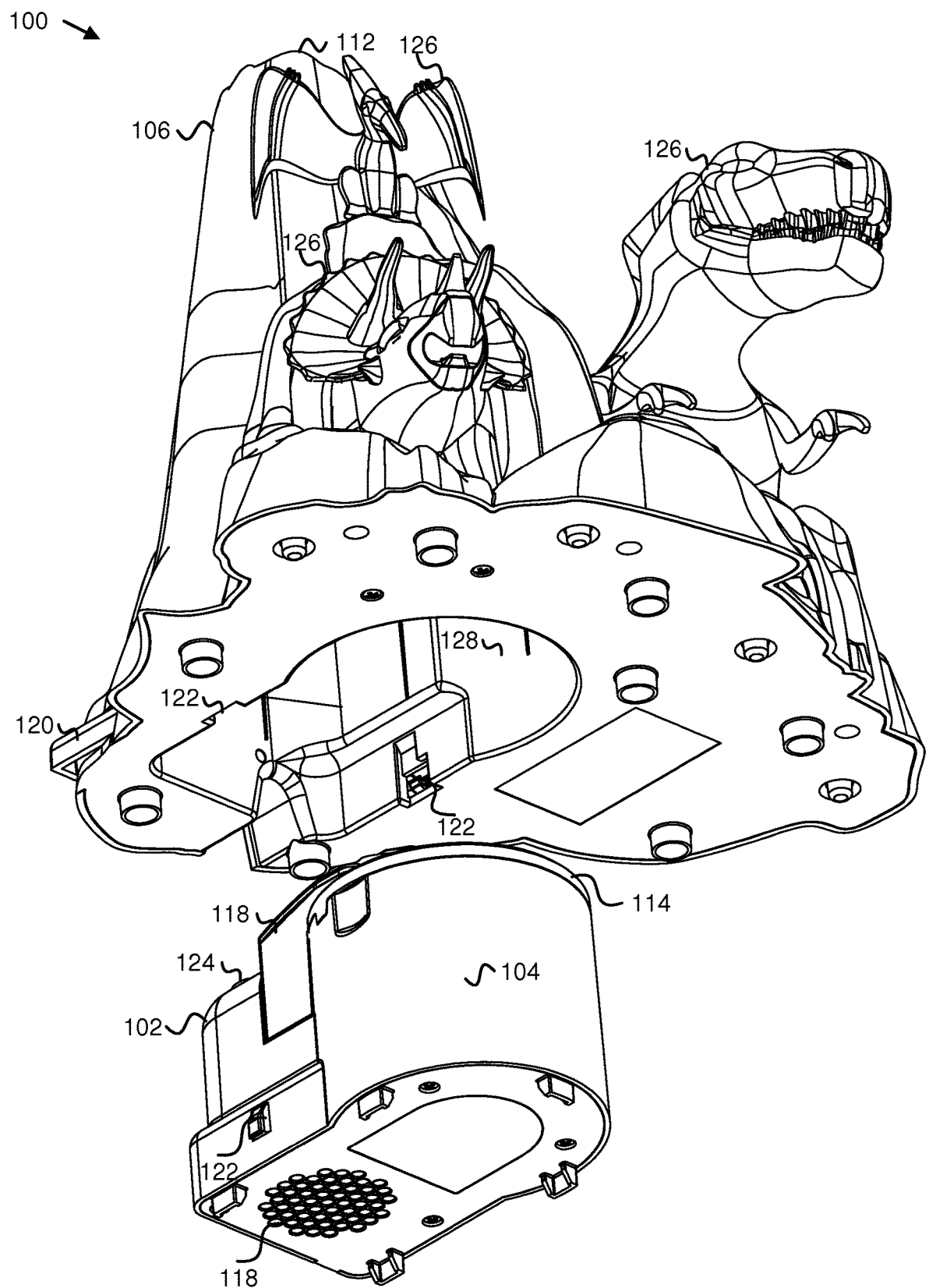
FIG. 1A is an exploded perspective view of one embodiment of a diffuser with an interchangeable cover.

Reference throughout this specification to "one embodiment," "an embodiment," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Aspects of the present disclosure are described below with reference to schematic flowchart diagrams and/or schematic block diagrams of methods, apparatuses, systems, and computer program products according to embodiments of the disclosure. It will be understood that each block of the schematic flowchart diagrams and/or schematic block diagrams, and combinations of blocks in the schematic flowchart diagrams and/or schematic block diagrams, can be implemented by computer program instructions. These computer program instructions may be provided to a processor of a computer or other programmable data processing apparatus to produce a machine, such that the instructions, which execute via the processor or other programmable data processing apparatus, create means for implementing the functions and/or acts specified in the schematic flowchart diagrams and/or schematic block diagrams block or blocks.

It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated figures. Although various arrow types and line types may be employed in the flowchart and/or block diagrams, they are understood not to limit the scope of the corresponding embodiments. For instance, an arrow may indicate a waiting or monitoring period of unspecified duration between enumerated steps of the depicted embodiment.

In the following detailed description, reference is made to the accompanying drawings, which form a part thereof. The foregoing summary is illustrative only and is not intended to be in any way limiting. In addition to the illustrative aspects, embodiments, and features described above, further aspects, embodiments, and features will become apparent by reference to the drawings and the following detailed description. The description of elements in each figure may refer to elements of proceeding figures. Like numbers may refer to like elements in the figures, including alternate embodiments of like elements.

FIG. 1A illustrates one embodiment of a system 100 comprising a diffuser 102 and an interchangeable and/or removable cover 106. The diffuser system 100, in certain embodiments, comprises one or more removable, interchangeable, detachable, replaceable, and/or swappable covers 106 or shrouds, which may allow a user to customize the diffuser system 100 with different shapes, designs, colors, features, decorations, or the like. For example, a cover 106 may be formed to resemble an object, design, scene, character, figurine, animal, vehicle, monster, sports item, seasonal item (e.g., Christmas, Thanksgiving, birthday, or the like), toy, or another design. For example, in the depicted embodiment, the cover 106 comprises a prehistoric scene with several dinosaur decorative features 126 and a volcano. In the embodiment described below with regard to FIG. 1B, the cover 106 comprises an underwater scene with decorative features 126 comprising several sea creatures.

The cover 106 may comprise one or more openings 112 (e.g., an outlet 112) in fluid communication with a diffuser stream 108 from a diffuser 102 (e.g., through an opening in a lid 114 of the diffuser 102 (e.g., an opening 116 as described below), through one or more internal channels of the cover 106 that receive and/or route the diffuser stream 108, or the like), allowing the diffuser stream 108 out of the cover 106 (e.g., to an exterior of the cover 106) where a user may inhale and/or smell the stream 108. A diffuser stream 108, as used herein, comprises a liquid dispersed into air. In certain embodiments, an air source 118 of the diffuser 102 moves or directs the diffuser stream 108 in a direction away from the diffuser 102, even without a cover 106 being installed on the diffuser 102. In the depicted embodiment, the diffuser 102 is not installed in the cover 106, but is operating independently to produce the diffuser stream 108 without providing the diffuser stream 108 to the cover 106.

The one or more decorative elements 126 of the cover 106, in certain embodiments, may comprise one or more interactive elements 126, such as a light, a speaker, a mechanical actuator, routing vents for the stream 108, a sensor, a button, a switch, or the like, with which a user may interact with the diffuser system 100. In a further embodiment, one or more interactive elements 126 and/or portions of an interactive element 126 may be part of the diffuser 102, so that it may be usable for different covers 106 (e.g., a speaker may be disposed on the diffuser 102, and may interface with an element of the cover 106, such as a mouth, a speaker grid, one or more openings, or the like).

The cover 106 and/or the diffuser 102, in certain embodiments, may comprise an electrical interface 124 comprising one or more electrical connections, allowing the one or more interactive elements 126 to receive electricity and/or control signals from the diffuser 102. For example, the diffuser 102 and/or the cover 106 may comprise a controller (e.g., an application specific integrated circuit (ASIC), a field programmable gate array (FPGA) or other programmable logic, or another integrated circuit device) which provides control signals and/or electrical power to one or more interactive elements 126 of the cover 106. The diffuser 102 may comprise an electrical interface 124 that is complementary to and/or compatible with an associated electrical interface 124 of one or more covers 106. For example, the diffuser 102 may comprise an electrical interface 124 with one or more electrical contacts 124 (e.g., one or more metallic pins, pads, ports, plugs, jacks, couplings, or the like) for electrical power and/or control signals that interface or electrically couple to one or more corresponding electrical contacts 124 of a cover 106.

The one or more interactive elements 126 may be selected from and/or integrated with one or more character or decorative elements 126 of the cover 106. For example, the stream 108 may be routed through eyes, ears, a nose, a mouth, a train's smoke stack, a volcano, a vehicle's exhaust pipe, or the like of different covers 106; headlights, eyes, stars, a moon, or another element of the cover 106 may comprise a light; a mouth, a horn, or the like may comprise a speaker; an arm, a leg, a tail, an animal, a wheel, a vehicle, a valve or vent, or other moving part may be moved by a mechanical actuator; or a cover 106 may comprise another interactive element 126. Although the interactive elements 126 may differ between different covers 106, in certain embodiments, different covers 106 comprise electrical interfaces 124 and/or diffuser stream interfaces compatible with the same diffuser 102. Different covers 106, in certain embodiments, may comprise different configurations, layouts, shapes, and/or positions of channels and/or outlets/openings 112. Certain covers 106 may comprise one or more valves or vents, for example, in fluid communication with an outlet 112 and/or opening 112, which may be mechanically actuated or otherwise moved to direct or force the stream 108 through different channels, outlets 112, and/or openings 112 of the same cover 106.

The controller may comprise and/or be in communication with a non-volatile memory (e.g., NAND flash memory, read-only memory (ROM), or the like), a volatile memory (e.g., random access memory (RAM)), or other non-transitory computer readable storage medium. The controller may store and retrieve data for one or more interactive elements 126, such as music, voice commands, sound effects, diffuser schedules, or the like, for use controlling and providing operations of the diffuser system 100. In certain embodiments, the diffuser 102 comprises one or more sensors (e.g., a button, an optical sensor, radio frequency identification (RFID), or the like) in communication with the controller, so that the controller may detect the presence of a cover 106, distinguish between different covers 106, determine capabilities or interactive elements 126 of an installed cover 106, or the like.

The cover 106, in the depicted embodiment, includes a cavity 128 shaped to receive and/or interface with the diffuser 102. The internal channel 302 extends between the cavity 128 and the opening/outlet 112. The cavity 128, in one embodiment, may be shaped substantially similar to an outside of the diffuser 102, only larger, in order to receive the diffuser 102. One or more coupling elements 122 may removably secure the diffuser 102 within the cavity 128. For example, the cover 106 may include a user interface 120 (e.g., a button, lever, switch, knob, dial, or the like) allowing a user to release and/or open one or more coupling elements 122 and remove the cover 106 from the diffuser 102. For example, in an embodiment where a coupling element 122 comprises a spring loaded latch allowing a user to release the cover 106 from the diffuser 102 by hand, without using a tool, the spring loaded latch may be biased in a closed or locked position by a spring, and the user may push or actuate a button 120 to open or release the spring loaded latch, or the like.

The cover 106 may be sized and shaped to house one or more internal components of the diffuser system 100, such as the diffuser 102, a diffuser chamber 104 comprising a diffuser element, an air source 118, a controller, or the like within the internal cavity 128 of the cover 106 (e.g., the cavity 128 may be shaped or otherwise configured to receive a removable diffuser 102 or the like). While outer shapes, decorative and/or interactive features, or the like of different covers 106 may differ, in certain embodiments, the different covers 106 may be shaped or formed to cover, house, couple to, and/or interface with the same internal components of the diffuser 102. The diffuser 102 may provide the diffuser stream 108, electrical power and/or control signals, or the like to covers 106 with different shapes and/or designs. A cover 106, in certain embodiments, may substantially enclose or cover all but a bottom side of the diffuser 102, other than the outlet 112 or the like (e.g., within a cavity 128 or other opening 128 in the cover 106).

Figure 1B:
FIG. 1B is a perspective view of one embodiment of a diffuser with an interchangeable cover.

FIG. 1B illustrates another embodiment of a system 130 comprising a diffuser 102 and an interchangeable and/or removable cover 106. The diffuser system 130, in certain embodiments, may comprise a diffuser 102 with a diffuser chamber 104 comprising a diffuser element, a lid 114 with an opening 116 or other outlet, an air source 118, a controller, electrical connections 110, a user interface 120, one or more coupling elements 122, an electrical interface 124 with a cover 106, and/or other components for providing the diffuser stream 108 and/or enabling interactive elements 126 of a cover 106. The diffuser stream 108 may comprise a dispersed liquid such as one or more of a vapor stream comprising one or more liquids (e.g., water, an essential oil, or the like) in a gas phase, droplets or particles of one or more liquids projected or condensed within the stream 108, a mist, an aerosol, or the like.

In one embodiment, the diffuser 102 and associated components are shaped and formed to resemble and/or actually be a miniaturized distillation plant, such as an essential oil distillery. For example, the diffuser chamber 104 may comprise or resemble a cooker; the air source 118 may comprise or resemble a boiler or other steam source; piping, tubing, or another channel may be disposed between the cooker and the boiler; or the like. Embodiments of the diffuser 102 resembling or comprising a distillation plant or distillery may be educational, especially for children, educating users on the distillation process and how essential oils or other distilled products are produced.

The diffuser chamber 104 may receive and/or store a liquid for diffusing, such as water, one or more essential oils, or the like. In certain embodiments, at least for educational purposes, or the like, the diffuser chamber 104 may receive solid plant material, such as leaves, stems, needles, roots, seeds, or the like. The diffuser chamber 104, in one embodiment, may distill or diffuse at least some amount of liquid, such as an essential oil or other liquid plant product, from the solid plant material, instead of or in addition to another liquid of the diffuser chamber 104. In other embodiments, the use of solid plant material may be purely educational, so that the diffuser 102 of the diffuser system 130 may be used to educate a user about the functionality of a distillation plant or essential oil distillery, even if the diffuser chamber 104 distills and/or diffuses little or no essential oil from the plant material. In a further embodiment, the diffuser chamber 104 receives only a liquid, and is not configured to receive solid plant material. The diffuser chamber 104 may be substantially sealed (e.g., liquid or water tight), other than a liquid input and/or a vapor stream output 118, or the like, when the lid 114 is properly installed, to protect other components of the diffuser 102, such as electrical components 110 or the like.

The diffuser 102, in one embodiment, comprises a complete diffuser 102. A complete diffuser 102, as used herein, comprises a diffuser 102 capable of providing a diffuser stream 108 of dispersed liquid away from the diffuser 102 independently, without installation of a cover 106. For example, a complete diffuser 102 may comprise a lid 114 or top with an opening 116 or other outlet for providing a diffuser stream 108, and a removable cover 106 may optionally be installed over the lid 114, allowing the complete diffuser 102 to operate with or without installation of the cover 106. Without a separate lid 114 to channel and/or direct air from the air source 118 into the diffuser stream 108, in certain embodiments, even if the diffuser 102 is powered and running, a dispersed liquid may remain in or around the diffuser chamber 104, without forming a diffuser stream 108. In embodiments where the diffuser 102 comprises a complete diffuser 102, the diffuser 102 may provide a diffuser stream 108 with or without a cover 106.

The diffuser system 130, in certain embodiments, may comprise a user interface 120, to allow a user to turn the diffuser system 130 on or off (e.g., start and stop the diffuser stream 108), to control or trigger an interactive element 126 (e.g., turn a light on or off, play a sound, move an actuator), to adjust a timing and/or intensity of the diffuser stream 108 (e.g., an intermittent or periodic timer, a shutoff timer, or the like), or to trigger another action. The user interface 120, in one embodiment, comprises a mechanical and/or electrical interface, with one or more buttons, switches, dials, optical sensors, touch sensors, screens, touch screens, keys, or the like. In a further embodiment, the user interface comprises a wireless module, allowing functions and/or actions of the diffuser system 130 to be controlled wirelessly, from a mobile device such as a mobile phone, from a computer, from a remote control, or the like. In one embodiment, the cover 106 comprises one or more user interface elements configured to pass through user input to the diffuser 102, such as a cutout or other opening allowing a user to access a user interface 120 element of the diffuser 102; a button, switch, or other user interface 120 element on the cover 106 may interface with a corresponding user interface 120 element on the diffuser 102; or the like.

The diffuser chamber 104, in certain embodiments, has a lid 114, which may be detachable, removable, or the like, allowing a user to add liquid (e.g., water and/or an essential oil) or the like. In another embodiment, the lid 114 may be permanently affixed to the diffuser chamber 104, and a user may add a liquid through the opening 116 or the like. The diffuser 102 and/or a cover 106 may comprise one or more coupling or securing elements 122 to removably couple a cover 106 to the diffuser 102. For example, in various embodiments, the diffuser 102 and/or a cover 106 may comprise one or more latches, lips or ledges, clips, snaps, hooks, threading, spring loaded latches, or the like, in a configuration to couple and/or secure a cover 106 to the diffuser 102.

The diffuser 102, in the depicted embodiment, comprises an air source 118. While the air source 118, in certain embodiments, may be outside of the diffuser chamber 104, in other embodiments, as described below, a diffuser element (e.g., the diffuser element 202 described below) or portion thereof may be disposed within the diffuser chamber 104, with a power source and/or one or more other electrical components disposed outside of the diffuser chamber 104 to power the diffuser element, or the like, while the air source 118 may provide an air current to move a diffused/dispersed liquid from the diffuser chamber 104.

The diffuser 102 may comprise a diffuser element 202 (e.g., an ultrasonic plate, a nebulizer), an air source 118 (e.g., a fan, a blower, a pump, or the like), and a diffuser chamber 104, together configured to disperse a liquid (e.g., water, an essential oil) into air to provide a diffuser stream 108. A cover 106, removably couplable to a diffuser 102 may comprise one or more channels and/or openings 112 that receive and route the diffuser stream 108 from the diffuser 102 as described above.

As described above, a cover 106 for a diffuser 102 may comprise an electrical interface 124 with the diffuser 102, and one or more interactive elements 126 of the cover 106 may be in electrical communication with the diffuser 102 through the electrical interface 124. For example, one or more interactive elements 126 may comprise a light, a speaker, a mechanical actuator, or the like. A mechanical actuator may comprise one or more valves that selectively direct a diffuser stream 108 through different channels or openings 112 of a cover 106.

The diffuser chamber 104 may hold a specific liquid or liquid mixture to be diffused. For example, the diffuser chamber 104 may store or contain an essential oil liquid, blend, and/or mixture. An essential oil liquid may include one or more essential oils, including a blend of two or more essential oils. In some embodiments, the diffuser chamber 104 holds a composition consisting essentially of essential oils. In another embodiment, the composition consists solely of essential oils. In a further embodiment, the composition may comprise water or another liquid and one or more essential oils.

An essential oil may be a substantially pure and uncut essential oil. Essential oils are naturally occurring aromatic liquids found in the roots, stems, bark, seeds, flowers, and other parts of plants. These oils are fat soluble, non-water-based phytochemicals that include volatile organic compounds. The chemistry of any particular essential oil can be very complex and may consist of hundreds of different and unique chemical compounds. In nature, these oils give plants their distinctive smells, provide protection against disease, and assist in pollination. When separated from their parent plant, essential oils in their pure form are translucent with colors ranging from clear to pink or blue.

The air source 118, in certain embodiments, comprises a fan, a blower, a pump, or the like that provides a current or stream of air that, when introduced into the diffuser chamber 104, carries a diffused/dispersed liquid out of the diffuser chamber 104 to form the diffuser stream 108. In a further embodiment, the air source 118 may comprise a heat source or other energy source, in thermal communication with the diffuser chamber 104. For example, the air source 118 may heat the current or stream of air, the current or stream of air from the air source 118 may comprise steam, or the like. In other embodiments, the current or stream of air from the air source 118 may comprise ambient air, at about room temperature, or the like. The air source 118 may comprise a nebulizer, may cooperate with an electric heating element, an ultrasonic plate, or another diffuser element within the diffuser chamber 104, to transfer the diffused/dispersed liquid out of the diffuser chamber 104 to create the diffuser stream 108, or the like. The air source 118, in one embodiment, resembles and/or comprises a distillery boiler (e.g., a miniaturized boiler). The diffuser 102 may comprise tubing, a pipe, or another channel between the air source 118 and the diffuser chamber 104, placing the air source 118 in fluid communication with the diffuser chamber 104, so that the air current or stream from the air source 118 may enter the diffuser chamber 104. For example, in the depicted embodiment, a portion of the lid 114 comprises a guide or channel of the air source 118, to direct air from the air source 118 into the diffuser chamber 104.

In one embodiment, the air source 118 provides a stream of warm, heated air, steam, water, or another fluid to the diffuser chamber 104. The diffuser chamber 104, in certain embodiments, may be sealed from the heated fluid stream so that the heated fluid stream from the heat source remain on the outside of the diffuser chamber 104, to prevent liquid from the diffuser chamber 104 from entering the air source 118. In various embodiments, a heated fluid stream (e.g., heated air, steam, or the like) may enter the diffuser chamber 104 from the air source 118; a diffuser element or a portion thereof may be disposed within the diffuser chamber 104, or the like, to evaporate and/or diffuse/disperse a liquid from the diffuser chamber 104 (e.g., an ultrasonic plate); a nebulizer may diffuser/disperse a liquid into air; or the like. In one embodiment, the diffuser chamber 104 and the air source 118 may be shaped and positioned to form a nebulizer (e.g., a jet nebulizer or atomizer), and the velocity of the air current or stream from the air source 118 flowing through the liquid in the diffuser chamber 104 to create an aerosol, mist, or the like, forming the diffuser stream 108 of dispersed liquid.

Figure 1C:
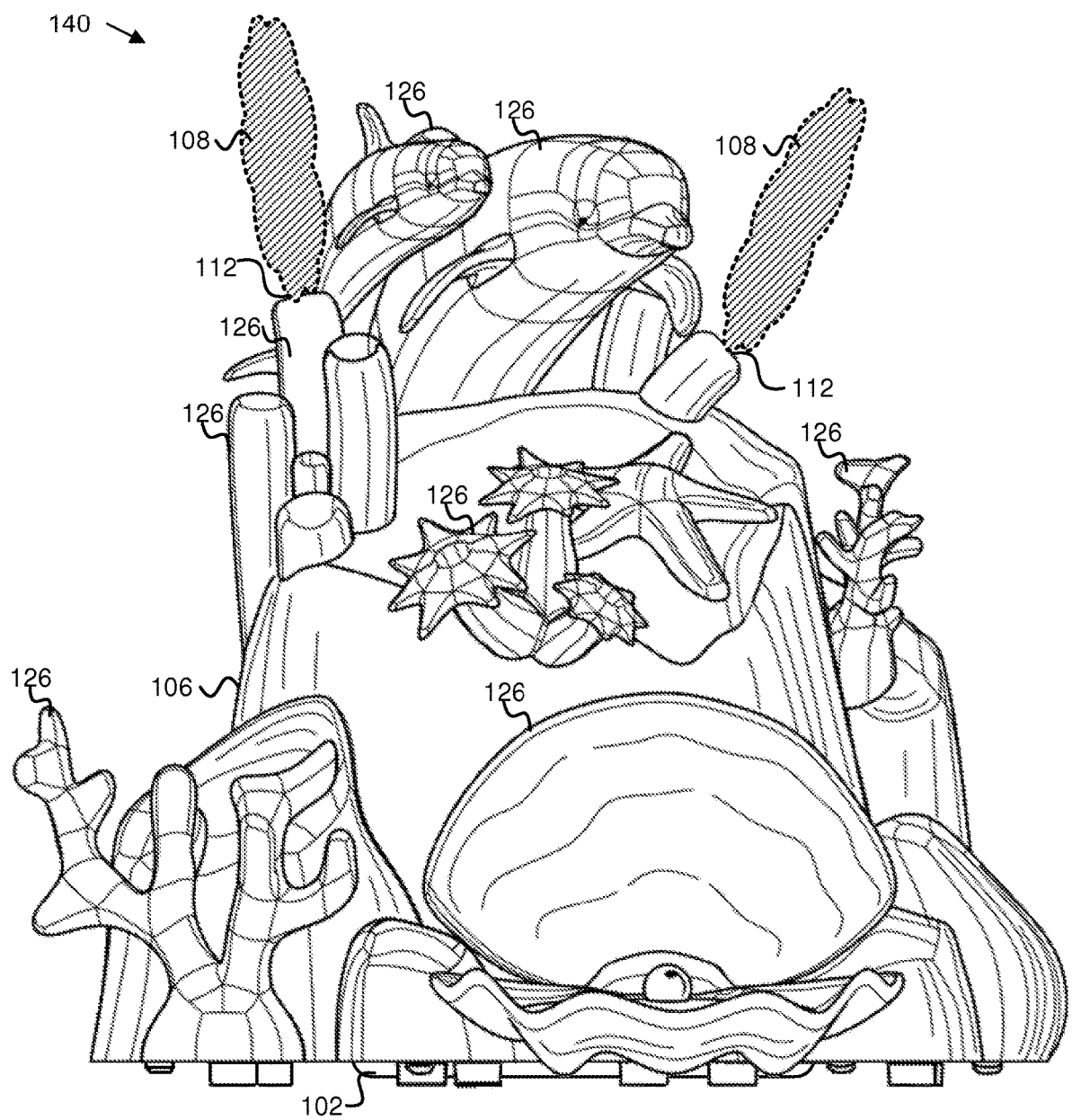
FIG. 1C is a front view of another embodiment of a diffuser with an interchangeable cover.

FIG. 1C illustrates a further embodiment of a system 140 comprising a diffuser 102 with an interchangeable cover 106 installed. In the depicted embodiment, the diffuser 102 is installed within a cavity or opening of the cover 106. The cover 106 interfaces with the opening 116 in the lid 114 of the diffuser, to receive dispersed liquid of a diffuser stream 108 from the diffuser 102. The cover 106, in the depicted embodiment, splits and routes the diffuser stream 108 through two different openings 112 or outlets 112, to provide the diffuser stream 108 to a user.

The cover 106 of FIG. 1C has different decorative features 126 than the cover 106 of FIG. 1A and FIG. 1B. However, in certain embodiments, both covers 106 may be compatible with the same diffuser 102. Although the covers 106 of FIG. 1A, FIG. 1B, and FIG. 1C may be compatible with the same diffuser 102, the different covers 106 may have different functionality (e.g., different decorative and/or interactive features 126, different lights, different sounds), may route the diffuser stream(s) 108 differently, or the like.

Figure 2A:
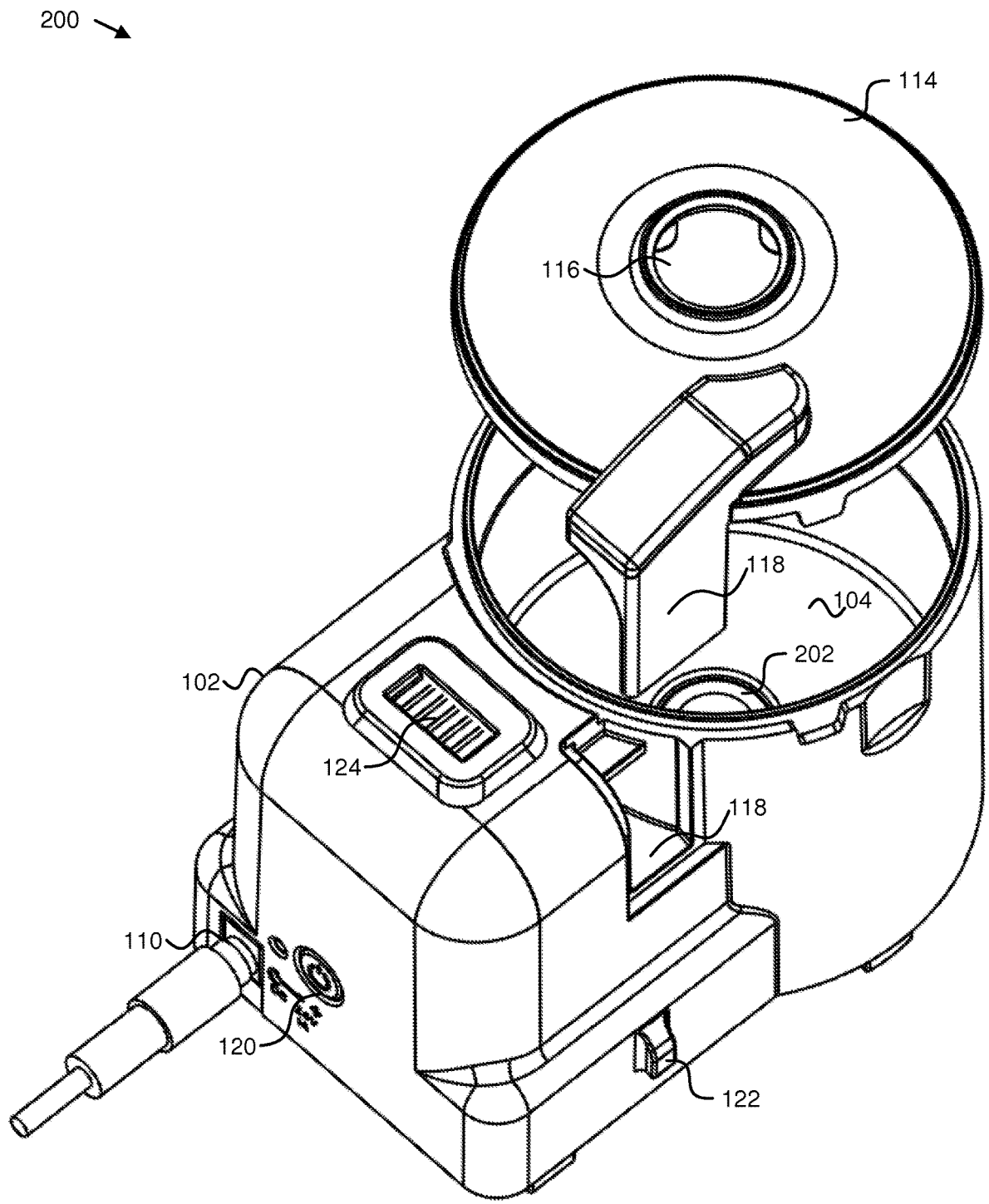
FIG. 2A is a perspective view of one embodiment of a complete diffuser with a lid.

FIG. 2A illustrates one embodiment 200 of a complete diffuser 102 with a lid 114. The complete diffuser 102 of FIG. 2A, in certain embodiments, may be substantially similar to the diffuser 102 described above with regard to FIGS. 1A and 1B. The complete diffuser 102, in the depicted embodiment, includes a diffuser element 202 comprising an ultrasonic plate within a diffuser chamber 104. The diffuser element 202, in other embodiments, may comprise a nebulizer (e.g., a jet nebulizer, an ultrasonic wave nebulizer, an ultrasonic vibrating mesh nebulizer, or the like), a humidifier (e.g., an evaporative humidifier, a vaporizer or warm mist humidifier, an impeller or cool mist humidifier, an ultrasonic humidifier, or the like), or another element 202 that disperses, diffuses, and/or evaporates a liquid into air. As described below with regard to the controller 212, in certain embodiments a controller of the complete diffuser 102 and/or a cover 106 may calibrate and/or adjust one or more settings of the diffuser element 202.

The lid 114, in the depicted embodiment, is removable, to facilitate the addition or removal of liquid in the diffuser cavity 114, cleaning and/or replacement of the diffuser element 202, and/or access to other elements of the complete diffuser 102. In other embodiments, the lid 114 may be permanently or semi-permanently affixed to the complete diffuser 102, and a liquid may be added or removed through the opening 116 in the lid 114.

The lid 114, in the depicted embodiment, includes a channel or guide portion of the air source 118, to guide an air stream from a fan, pump, blower, or the like of the air source 118 into the diffuser chamber 104, thereby forcing a diffuser stream 108 of liquid dispersed in air through the opening 116 in the lid 114. In other embodiments, the diffuser chamber 104 may comprise one or more openings, channels, and/or guides of the air source 118. The lid 114, in the depicted embodiment, has a single orientation or alignment with which the lid 114 fits on and interfaces with the complete diffuser 102 and/or the diffuser chamber 104. Because the lid 114, in the depicted embodiment, is shaped and formed to create a diffuser stream 108, allowing the complete diffuser 102 to operate with our without an installed cover 106, the cover 106, in certain embodiments, may be decorative, educational, and/or interactive, routing, receiving, and/or providing a diffuser stream 108 but not providing diffusing functions itself separate from the complete diffuser 102.

Figure 2B:
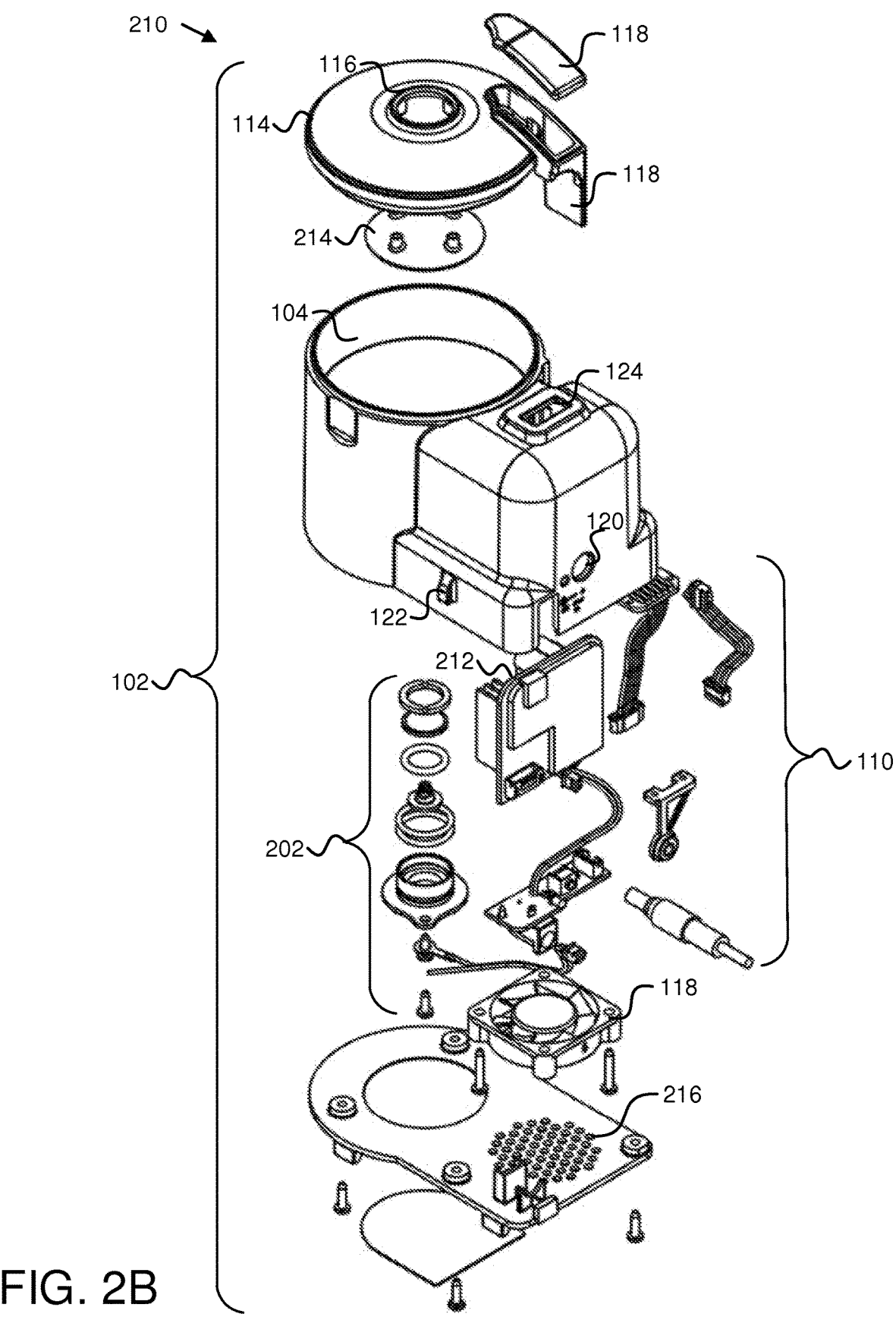
FIG. 2B is an exploded view of one embodiment of a complete diffuser with a lid.

FIG. 2B depicts an exploded view 210 of one embodiment of a complete diffuser 102 with a lid 114. The complete diffuser 102, in certain embodiments, may be substantially similar to one or more of the diffusers 102 described above with regard to FIGS. 1A, 1B, and/or 2A.

The complete diffuser 102, in the depicted embodiment, includes a controller 212 installed on a printed circuit board, powered by and/or in electrical communication with the one or more electrical connections 110. The controller 212 may comprise an application specific integrated circuit (ASIC), a field programmable gate array (FPGA) or other programmable logic, or another integrated circuit device, microcode for execution on a microprocessor or other embedded processor, firmware for an FPGA or other programmable logic, a processor and/or computer executable code stored on a non-transitory computer readable storage medium, or the like. The controller 212 is described in greater detail below with regard to FIG. 5.

The controller 212, in various embodiments, may control and/or receive user input from one or more interactive elements 126 of a cover 106 (e.g., through an electronic interface 124), may send and/or receive wireless communications comprising user input or other controls, may control operation of a diffuser element 202 and/or an air source 118, may calibrate and/or adjust settings for a diffuser element 202, and/or may perform one or more other functions for the complete diffuser 102 and/or a cover 106. While the controller 212 is depicted as part of the complete diffuser 102, in other embodiments, the controller 212 may be disposed in a cover 106, two or more different controllers 212 may be disposed in the complete diffuser 102 and a cover 106 (e.g., in communication using the electrical interface 124), or the like.

The lid 114, in the depicted embodiment, includes a splash guard 214. The splash guard 214 may allow a diffuser stream 108 to exit the lid 114 through the opening 116 while reducing or presenting a liquid from spilling out of the opening 116. In another embodiment, the lid may comprise a pressure valve, a one-way valve, or the like instead of or in addition to a splash guard 214. The splash guard 214, a valve, or the like may allow the diffuser stream 108 to exit the diffuser chamber 104 under pressure provided by the air source 118 but may prevent or slow the liquid from spilling out of the diffuser chamber 104 if the diffuser 102 is tipped or overturned during use, while the diffuser 102 is powered off, or the like.

A base plate or bottom of the complete diffuser 102, in the depicted embodiment, includes one or more openings 216 (e.g., a grate, a grid, mesh, an array of holes) through which the air source 118 may draw in air from outside the complete diffuser 102. The one or more openings 216 may be located in a location which remains outside of a cover 106 when the cover 106 is installed, so that the air source 118 may continue to draw in air.

Figure 3A:
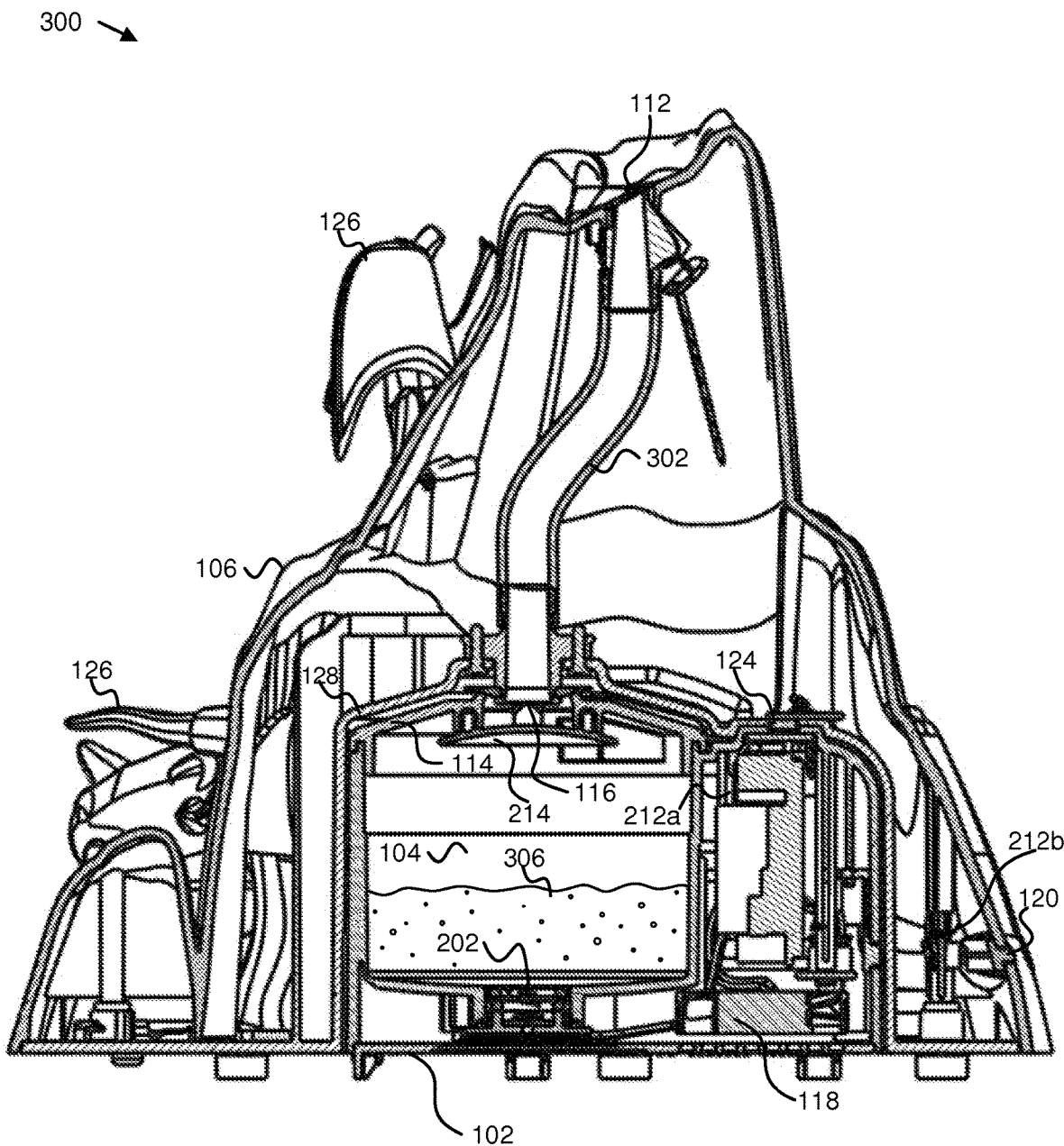
FIG. 3A is a cutaway side view of one embodiment of a diffuser with an interchangeable cover.

FIG. 3A illustrates a cutaway side view 300 of one embodiment of a diffuser 102 with an interchangeable cover 106. The cover 106, in the depicted embodiment, includes one or more internal channels 302, which receive a diffuser stream 108 (e.g., a liquid dispersed in air) from the diffuser 102 and route and/or channel the diffuser stream 108 to one or more openings/outlets 112 of the cover 106. A channel 302 of a cover 106 may comprise a tube, a pipe, a cavity, an internal wall of the cover 106, or the like. In certain embodiments, the cover 106 comprises multiple channels 302; a T shaped, Y shaped, or other split channel; or the like to route or direct the diffuser stream 108 to multiple openings/outlets 112. In a further embodiment, a channel 302 may include a valve with an electrical and/or mechanical actuator, or the like, to alternate routing of the diffuser stream 108 through different channels 302 and/or openings/outlets 112. A diffuser stream 108 routing valve may be controlled mechanically by a lever and/or switch actuated by a user, may be controlled electrically by a controller 212 (e.g., based on a timer, in response to user input, and/or in response to another trigger).

The cover 106, in the depicted embodiment, includes a cavity 128 shaped to receive and/or interface with the diffuser 102. The internal channel 302 extends between the cavity 128 and the opening/outlet 112. The cavity 128, in one embodiment, may be shaped substantially similar to an outside of the diffuser 102, only larger, in order to receive the diffuser 102. One or more coupling elements 122 may removably secure the diffuser 102 within the cavity 128. For example, the cover 106 may include a user interface 120 (e.g., a button, lever, switch, knob, dial, or the like) allowing a user to release and/or open one or more coupling elements 122 and remove the cover 106 from the diffuser 102. For example, in an embodiment where a coupling element 122 comprises a spring loaded latch allowing a user to release the cover 106 from the diffuser 102 by hand, without using a tool, the spring loaded latch may be biased in a closed or locked position by a spring, and the user may push or actuate a button 120 to open or release the spring loaded latch, or the like.

An inlet of the cavity 128 and/or an outlet/opening 116 of the diffuser 102, in certain embodiments, may include a seal (e.g., an O-ring, a gasket, or the like) to prevent a liquid 306 (e.g., water, an essential oil, or the like) and/or a diffuser stream 108 from escaping or leaking out of the diffuser 102 into the cavity 128, other than through the channel 302, the opening/outlet 112, or the like.

In the depicted embodiment, the diffuser 102 comprises a diffuser controller 212a and the cover 106 comprises a cover controller 212b. The diffuser controller 212a may be in communication with the cover controller 212b (and vice versa) over the electrical interface 124. In one embodiment, the diffuser controller 212a may detect the presence of and/or proper installation of a cover 106. For example, the diffuser controller 212a may detect that two contacts of the electrical interface 124 are short circuited in response to a cover 106 being installed, may receive a communication (e.g., a predefined code, an acknowledgment, or the like) from the cover controller 212b, or the like. The diffuser controller 212a and the cover controller 212b may cooperate to perform the functions described below with regard to the controller 212 of FIG. 5.

An external interface 110 may comprise an electrical interface 110 for receiving electric power, a liquid interface for receiving a liquid, a heated fluid stream interface for receiving a heated fluid stream, or the like from a source external to the diffuser 120 and/or the cover 106. The user interface 120 may comprise one or more buttons, switches, dials, optical sensors, touch sensors, screens, touch screens, keys, or the like to turn the diffuser 102 on or off, set a timer or period for the diffuser stream 108, interact with an interactive element 126, or the like.

For example, in certain embodiments, the user interface 120 may comprise a power button 120. In response to a user pushing the power button 120 once, or another predetermined number of times, power may come on at full power (e.g., may provide a diffuser stream 108 as "smoke" from the volcano for about 2.5-3 hours or the like), an LED or other light of the/user interface 120 may turn on green, a light or other interactive element 126 may be activated at the outlet 112 to light or otherwise interact with the diffuser stream 108, a light under the diffuser 102 may turn on, or the like.

In response to a user pressing the power button 120 a second time, or another predetermined number of times, power to the diffuser 102 may transition to intermittent mode (e.g., about 30 seconds on and about 30 seconds off, or another duty cycle), an LED or other light of the user interface 120 may turn red, or the like. In response to a user pressing the power button 120 a third time, or another predetermined number of times, power to the diffuser 102 may be turned off. In response to a user holding a power button 120 for 5 seconds or another predefined period, a light under the diffuser 102 may turn off, in response to a user holding a power button 120 for 5 additional seconds or another predefined period, the light under the diffuser 102 may turn back on, or the like.

In a further embodiment, in response to a user pressing the power button 120 a first time, the diffuser stream 108 is initiated and one or more lights are turned on (e.g., a bottom glow light below the diffuser 102, an outlet light at the outlet 112, or the like) and in response to a user pressing the power button 120 a second time, the diffuser stream 108 may be stopped and the one or more lights turned off. In certain embodiments, a separate light button 120 or other user interface element 120 may change the color of a light, may turn a specific light on or off, may turn another light on or off in response to being held down for a predefined period of time, or the like.

The user interface 120 may comprise a button or other interface to control an additional light (e.g., a light near an outlet 112 or the like), in addition to a power light, or the like. For example, the button or other interface may turn the additional light on with one press, turn to a different color (e.g., green) with a second press, turn to a different color (e.g., blue) with a third press, turn to a different color (e.g., red) with a fourth press, cycle through a series of multiple colors with a fifth press, turn off with a sixth press, or may cycle through a different series of lighting functions in response to a predefined number of presses.

In certain embodiments, certain elements of the diffuser 102 and/or the cover 106 may be replaceable by a user. For example, an ultrasonic plate assembly 202 or other diffuser element 202 may be replaceable using a key or another tool. One or more replaceable components may extend a life of the diffuser 102 and/or the cover 106.

Figure 3B:
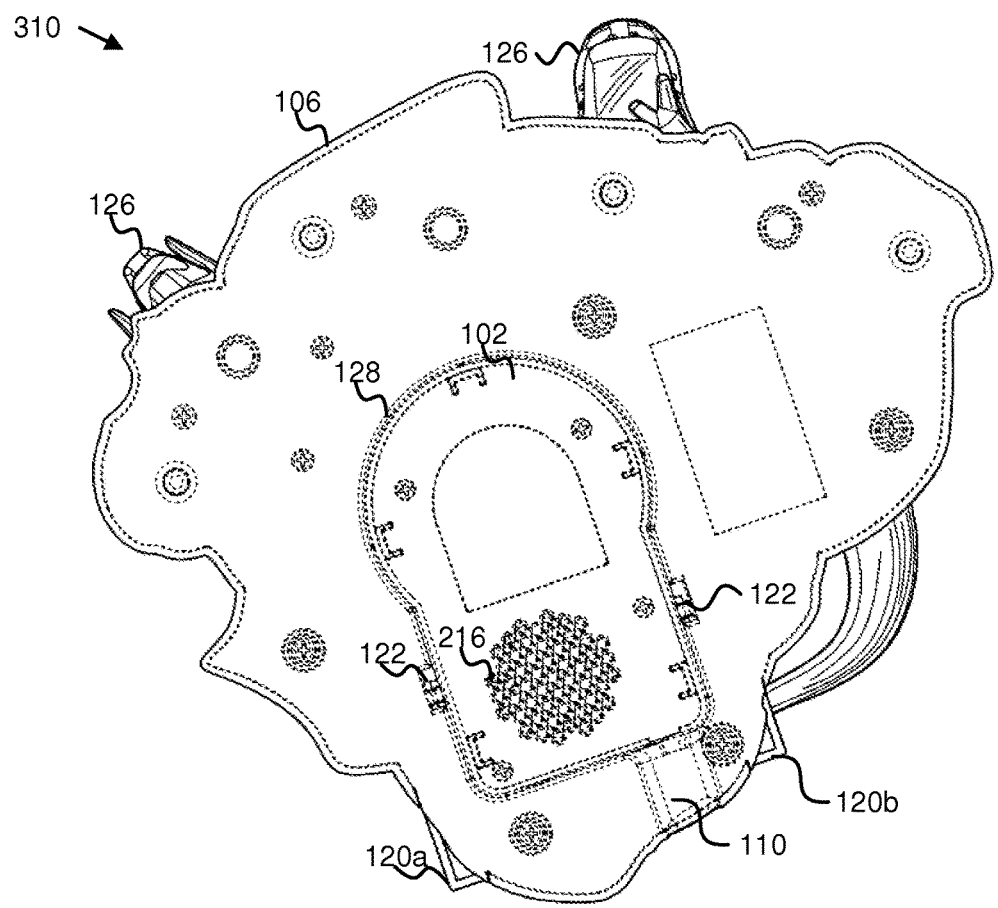
FIG. 3B is a bottom view of one embodiment of a diffuser with an interchangeable cover.

FIG. 3B is a bottom view 310 of one embodiment of a diffuser 102 with an interchangeable cover 106. In one embodiment, the user interface 120 may control and/or actuate a coupling element 122 allowing a user to separate and/or remove the cover 106 from the diffuser 102 by hand without requiring a key, a screwdriver, an Allen wrench, or another tool. For example, in the depicted embodiment, the user interface 120 comprises two button or slider mechanisms 120a, 120b, which a user may press to release a locking or coupling mechanism 122 between the cover 106 and the diffuser 102, allowing the diffuser 102 to be removed from the cover 106. For example, the coupling element 122 may comprise two loaded latches 122 (e.g., on opposite sides of the cavity 128), which are biased or pulled by a spring into a closed or locked position securing the diffuser 102 within the cavity 128 of the cover 106 by engaging two corresponding posts, ledges, walls, openings, or other coupling elements 122 on the diffuser 102. The first button 120a may be pressed to open/release a first spring loaded latch 122 and the second button 120b may be pressed to open/release a second spring loaded latch 122, allowing the diffuser 102 and/or the cover 106 to be removed.

Removing the cover 106 from the diffuser 102, in certain embodiments, allows a user to add a liquid (e.g., water, an essential oil) to the diffuser chamber 104, allows a user to use a different cover 106 with the same diffuser 102, or the like. In a further embodiment, the diffuser 102 may operate independently of a cover 106, and the diffuser 102 itself may be used to provide a diffuser stream 108, used as a toy or the like, used to educate a user regarding the operation of a distillation plant or essential oil distillery, with the cover 106 removed. Similarly, in certain embodiments, a cover 106 may be used independently as a toy, figurine, and/or decoration, without a diffuser 102 installed.

Figure 3C:
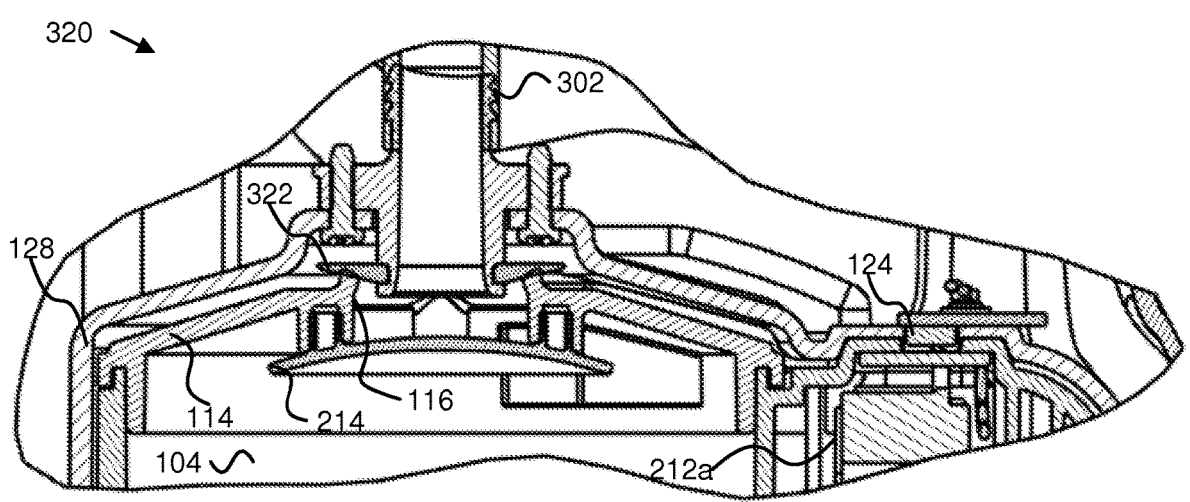
FIG. 3C is a magnified cutaway side view of one embodiment of an interface between a diffuser and an interchangeable cover.

FIG. 3C is a cutaway side view of one embodiment of an interface 320 between a diffuser 102 and an interchangeable cover 106. The interface 320, in the depicted embodiment, includes a seal 322. The seal 322 is disposed between the inlet of the cavity 128 into the channel 302 and the outlet/opening 116 of the diffuser 102. The seal 322 may comprise rubber, silicone, a plastic or polymer, or the like, such as an O-ring, a gasket, or the like. The seal 322, in certain embodiments, may prevent or limit a liquid 306 (e.g., water, an essential oil, or the like) and/or a diffuser stream 108 from escaping or leaking out of the diffuser 102 into the cavity 128, other than through the channel 302, the opening/outlet 112, or the like. The seal 322 may be a press fit, may be engaged by threading, a quarter turn lock, and/or another coupling 122 between the diffuser 102 and a cover 106.

Figure 4A:
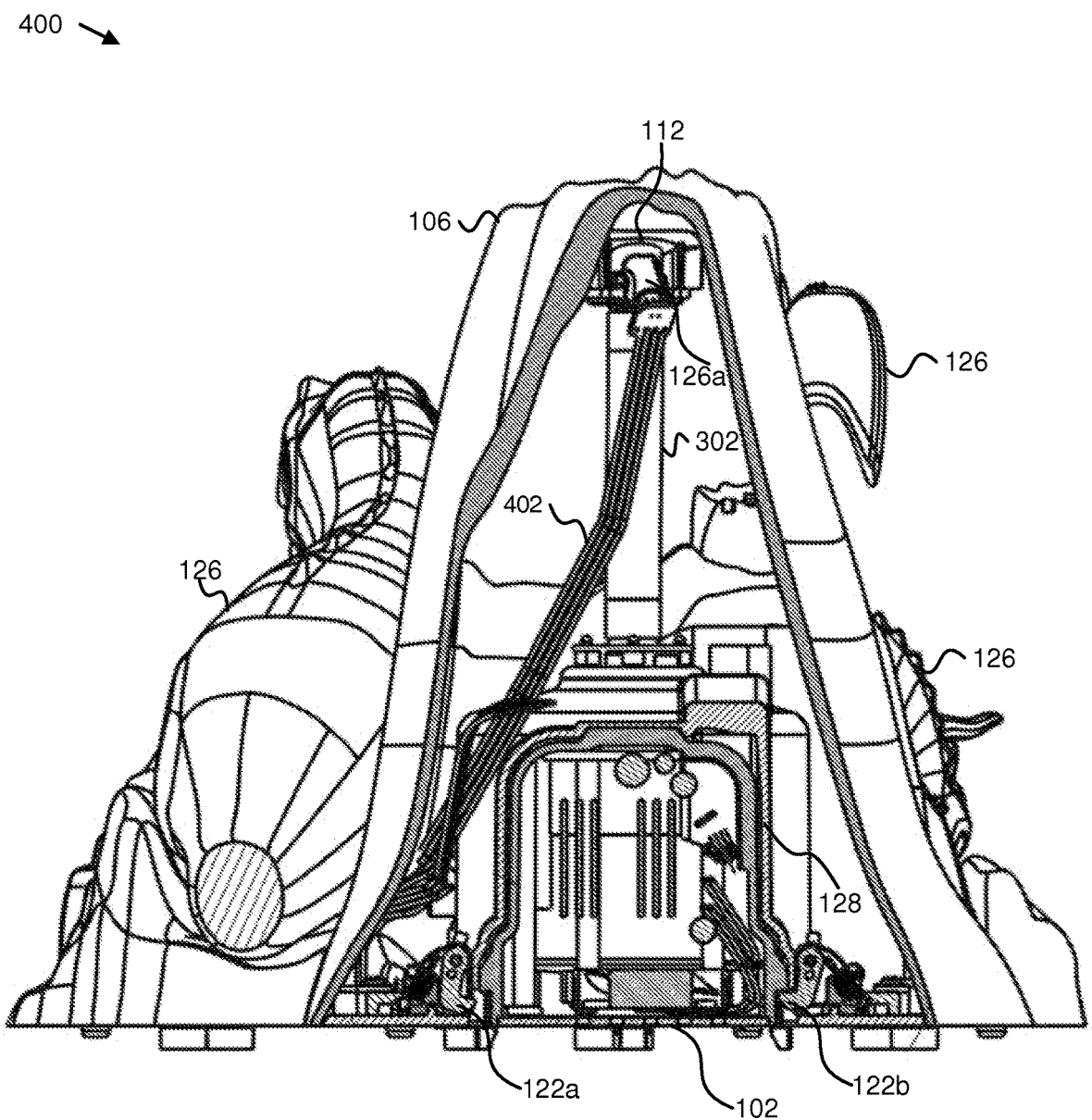
FIG. 4A is a cutaway rear view of one embodiment of a diffuser with an interchangeable cover.

FIG. 4A is a cutaway rear view 400 of one embodiment of a diffuser 102 with an interchangeable cover 106. The cover 106, in the depicted embodiment, includes cover electrical connections 402, providing electrical power from the diffuser 102 and/or control signals from a controller 212 to one or more interactive elements 126a of the cover 106, such as a light 126a disposed at an outlet/opening 112 of the cover 106 (e.g., to illuminate the diffuser stream 108), a speaker 126a, a mechanical actuator 126a to move an interactive element 126, a screen 126a, or another electronic interactive element 126a.

The cover 106, in the depicted embodiment, includes two opposing spring loaded latches 122a, 122b to removably secure and/or couple the diffuser 102 within the cavity 128 of the cover 106. One embodiment of spring loaded latches 122a, 122b are described below with regard to FIGS. 4A and 4B.

Figure 4B:
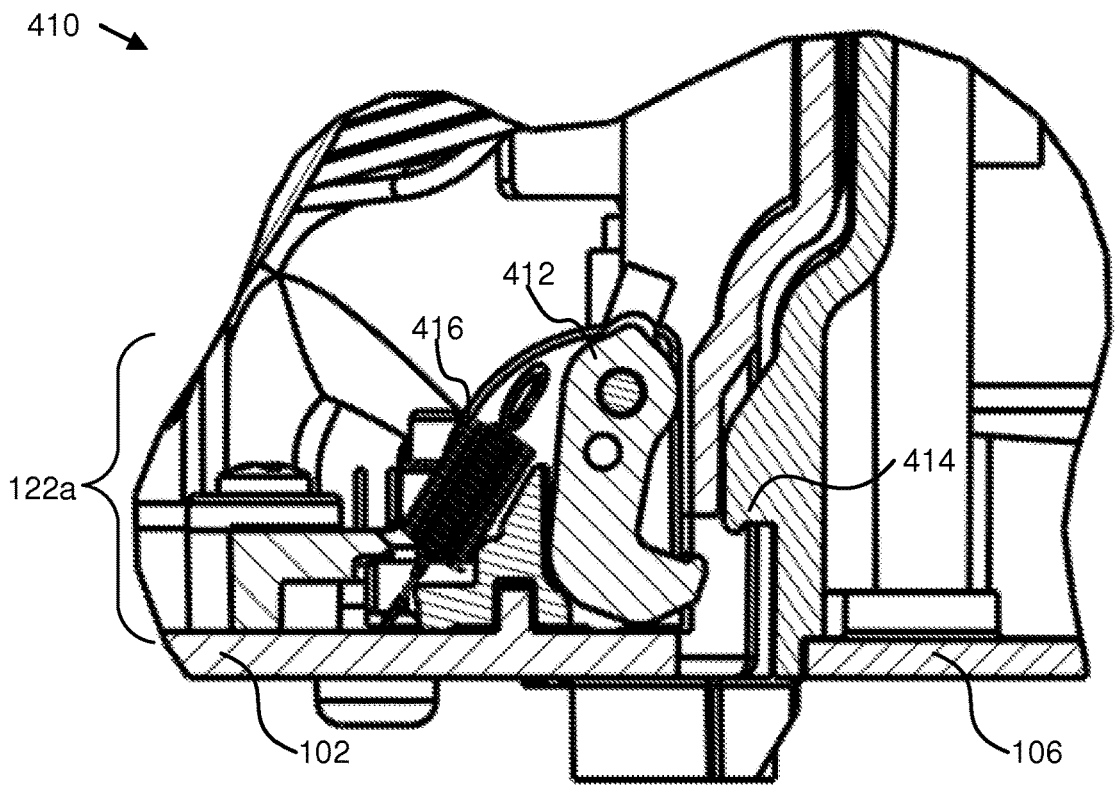
FIG. 4B is a magnified cutaway view of one embodiment of an open coupling between a diffuser and an interchangeable cover.
Figure 4C:
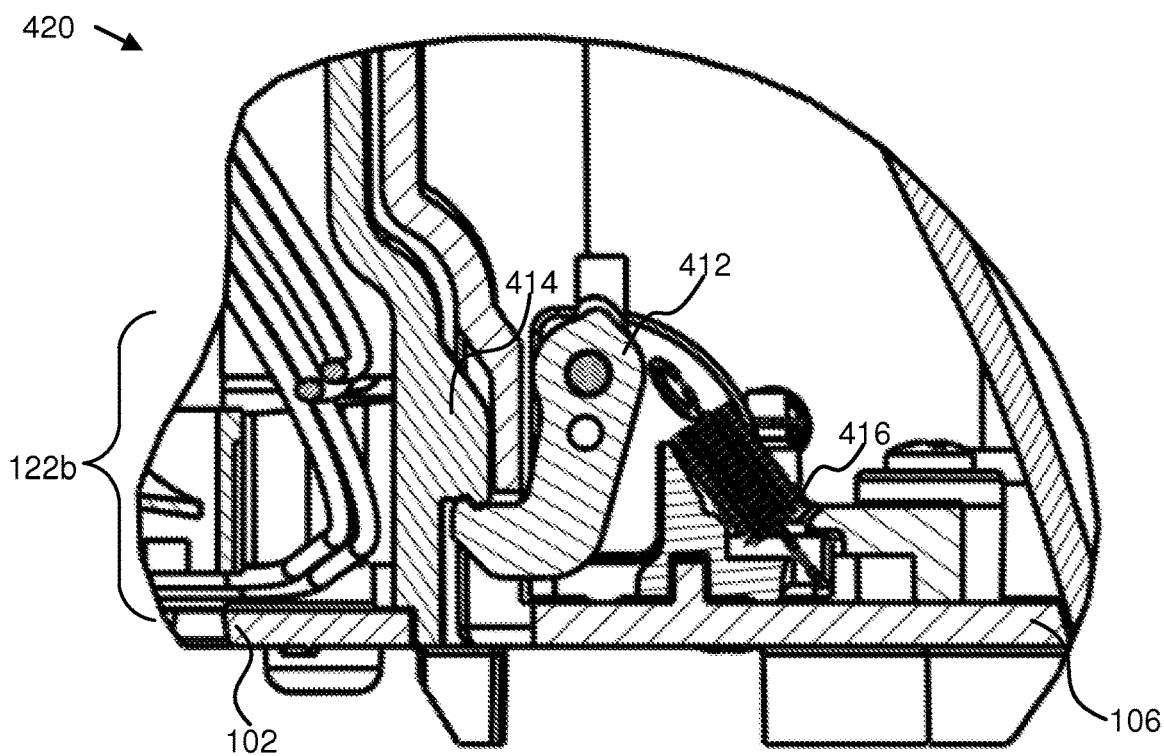
FIG. 4C is a magnified cutaway view of one embodiment of a closed coupling between a diffuser and an interchangeable cover.

FIG. 4B is a magnified cutaway view 410 of one embodiment of an open coupling 122a between a diffuser 102 and an interchangeable cover 106 and FIG. 4C is a magnified cutaway view 420 of one embodiment of a closed coupling 122b between a diffuser 102 and an interchangeable cover 106. The couplings 122a, 122b include a latch 412 shaped to interface with and/or be received by a post 414 extending from a wall of the diffuser 102 and a spring 416. In a default or resting position, the spring 416 exerts a force on an upper end of the latch 412 to rotate and/or pivot the latch 412 about an axis (e.g., a fulcrum) and to extend an opposite, bottom end of the latch 412 toward the post 414 of the diffuser 102 to lock and/or secure the diffuser 102 within the cavity 128 of the cover 106.

In response to a user pushing a button 120a, 120b or triggering another user interface element 120, the force of the button 120a, 120b being pushed or the other trigger causes the latch 412 to rotate about the axis in an opposite direction, against the spring 416 (e.g., stretching the spring 416), so that the bottom end of the latch 412 rotates away from the post 414 thereby releasing the post 414 and the diffuser 102. A coupling 122a, 122b, in certain embodiments, may comprise a sliding, spring loaded coupling, with a button 120a, 120b sliding along a track to actuate the latch 412, with the spring biasing the button 120a, 120b into an extended/un-pressed position and biasing the latch 412 into a closed/locked position. Other embodiments may comprise one or more different couplings, such as threading, a quarter-turn lock, another type of latch or hook, a press fit, or the like.

Figure 5:
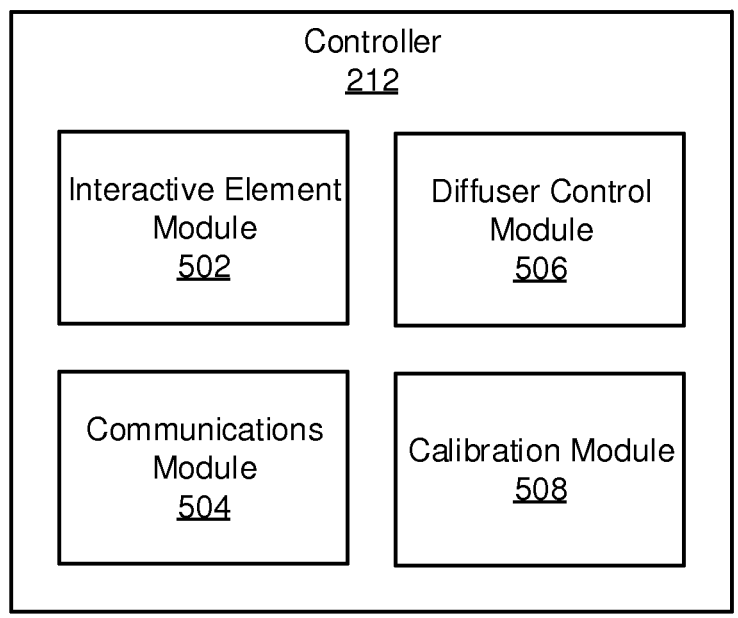
FIG. 5 is a schematic block diagram illustrating one embodiment of a controller for a diffuser with an interchangeable cover.

FIG. 5 is a schematic block diagram illustrating one embodiment of a controller 212 for a diffuser 102 with an interchangeable cover 106. As described above, the controller 212 may comprise a diffuser controller 212a disposed in the diffuser 102, a cover controller 212b disposed in a cover 106, a combination of both a diffuser controller 212a and a cover controller 212b, or the like. The controller 212 may comprise an application specific integrated circuit (ASIC), a field programmable gate array (FPGA) or other programmable logic, or another integrated circuit device, microcode for execution on a microprocessor or other embedded processor, firmware for an FPGA or other programmable logic, a processor and/or computer executable code stored on a non-transitory computer readable storage medium, or the like. In the depicted embodiment, the controller 212 includes an interactive element module 502, a communications module 504, a diffuser controller module 506, and a calibration module 508.

Aspects of the present disclosure may be embodied as an apparatus, system, method, or computer program product. Accordingly, aspects of the present disclosure may take the form of an entirely hardware embodiment, an entirely software embodiment (including firmware, resident software, micro-code, or the like) or an embodiment combining software and hardware aspects that may all generally be referred to herein as a "circuit," "module," "apparatus," or "system." Furthermore, aspects of the present disclosure may take the form of a computer program product embodied in one or more non-transitory computer readable storage media storing computer readable and/or executable program code.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, or the like.

Modules may also be implemented at least partially in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may include a single instruction, or many instructions, and may even be distributed over several different code segments, among different programs, across several memory devices, or the like. Where a module or portions of a module are implemented in software, the software portions may be stored on one or more computer readable and/or executable storage media. Any combination of one or more computer readable storage media may be utilized. A computer readable storage medium may include, for example, but not limited to, an electronic, magnetic, optical, electromagnetic, infrared, or semiconductor system, apparatus, or device, or any suitable combination of the foregoing, but would not include propagating signals. In the context of this document, a computer readable and/or executable storage medium may be any tangible and/or non-transitory medium that may contain or store a program for use by or in connection with an instruction execution system, apparatus, processor, or device.

Computer program code for carrying out operations for aspects of the present disclosure may be written in any combination of one or more programming languages, including an object oriented programming language such as Python, Java, Smalltalk, C++, C #, Objective C, or the like, conventional procedural programming languages, such as the "C" programming language, scripting programming languages, and/or other similar programming languages. The program code may execute partly or entirely on one or more of a user's computer and/or on a remote computer or server over a data network or the like.

A component, as used herein, comprises a tangible, physical, non-transitory device. For example, a component may be implemented as a hardware logic circuit comprising custom VLSI circuits, gate arrays, or other integrated circuits; off-the-shelf semiconductors such as logic chips, transistors, or other discrete devices; and/or other mechanical or electrical devices. A component may also be implemented in programmable hardware devices such as field programmable gate arrays, programmable array logic, programmable logic devices, or the like. A component may comprise one or more silicon integrated circuit devices (e.g., chips, die, die planes, packages) or other discrete electrical devices, in electrical communication with one or more other components through electrical lines of a printed circuit board (PCB) or the like. Each of the modules described herein, in certain embodiments, may alternatively be embodied by or implemented as a component.

In one embodiment, the interactive element module 502 is configured to provide control signals and/or electrical power from the diffuser 102 (e.g., from the controller 212 of the diffuser 102) to one or more interactive elements 126 of a cover 106 using an electrical interface 124 of the cover 106. For example, the interactive element module 502 may turn a light element 126 (e.g., LED, incandescent, fluorescent) on or off; may manipulate a valve or vent to change a route for a diffuser stream 108; may play music, a sound effect, or another noise; may activate a mechanical actuator to move an interactive element 126 (e.g., an arm, a leg, a tail, an animal, a wheel, a vehicle, a valve or vent, or other moving part); or may otherwise control an interactive element 126 of a cover 106. In a further embodiment, the interactive element module 502 may be configured to provide control signals and/or electrical power to one or more interactive elements 126 on the diffuser 102, instead of and/or in addition to controlling interactive elements 126 of a cover 106.

The interactive element module 502 may provide control signals, electric power, or the like to an interactive element 126 using one or more wires, traces of a printed circuit board (PCB), or the like, connected to an electrical interface 124 of the diffuser 102 (e.g., one or more electrical pins, pads, or other contacts; an electrical plug or other coupling), which in turn may be electrically coupled to a complementary electrical interface 124 of a cover 106. A cover 106 may comprise one or more conductors 402 (e.g., internal wiring or the like) from an electrical interface 124 of the cover 106 (e.g., electrically interfaced with a diffuser 102) to one or more interactive elements 126.

The interactive element module 502, in certain embodiments, may be configured to control one or more interactive elements 126 based on user input received by the communications module 504, based on a predefined schedule, based on a timer, and/or based on another predefined trigger or event. The interactive element module 502, in a further embodiment, may control one or more interactive elements 126 based on a determination by the communications module 504 of which cover 106 is installed on the diffuser 102, of which interactive elements 126 an installed cover 106 comprises, or the like, customizing interactions to different covers 106.

The interactive element module 502, the communications module 504, the diffuser control module 506, and/or the calibration module 508, in one embodiment, may comprise and/or be in communication with a non-volatile memory (e.g., NAND flash memory, read-only memory (ROM), or the like), a volatile memory (e.g., random access memory (RAM)), or other non-transitory computer readable storage medium. The interactive element module 502 may store and retrieve data for one or more interactive elements 126, such as music, voice commands, sound effects, diffuser schedules, or the like, for use controlling and providing operations of the one or more interactive elements 126. As described below, in certain embodiments, the communications module 504 may dynamically store data from a user, for use by the interactive element module 502.

The interactive element module 502 may use different stored data (e.g., different sounds or the like) for different covers 106. For example, in an embodiment where different covers 106 represent different animals, the interactive element module 502 may select a different animal sound to play using a speaker, based on the animal type of the installed cover 106. In certain embodiments, the diffuser 102 comprises one or more sensors (e.g., a button, an optical sensor, radio frequency identification (RFID), a near field communications (NFC) reader or the like) in communication with the controller, so that the controller may detect the presence of a cover 106, distinguish between different covers 106, determine capabilities or interactive elements 126 of an installed cover 106, or the like.

In one embodiment, the communications module 504 is configured to receive user input and/or other data. For example, the communications module 504 may receive wireless signals comprising user input, so that the interactive element module 502 may provide control signals based on the user input. The communications module 504, in various embodiments, may comprise one or more of an infrared receiver or sensor, a radio frequency receiver, a Wi-Fi module, a Bluetooth module, a near field communication (NFC) module, a radio frequency identification (RFID) module, a microphone, a motion sensor, a data port (e.g., universal serial bus (USB), serial port, Ethernet port or other network port, or the like), and/or another receiver, transmitter, or transceiver.

The communications module 504 may receive commands, instructions, a schedule, a trigger, or other user input for the interactive element module 502 and/or the diffuser control module 506. For example, the communications module 504 may receive user input allowing a user to turn the diffuser 102 and or a diffuser cover 106 on and off (e.g., start and stop the diffuser stream 108), to control or trigger an interactive element 126, to adjust a timing and/or intensity of the diffuser stream 108 (e.g., an intermittent or periodic timer, a shutoff timer, or the like), or to trigger another action. The communications module 504, in one embodiment, comprises a mechanical and/or electrical user interface, with one or more buttons, switches, dials, optical sensors, touch sensors, screens, touch screens, keys, or the like. In a further embodiment, the communications module 504 comprises a wireless module, allowing functions and/or actions of the diffuser 102 and/or a cover 106 to be controlled wirelessly, from a mobile device such as a mobile phone, from a computer, from a remote control, or the like.

In one embodiment, the diffuser control module 506 is configured to control operation of a diffuser element. For example, in various embodiments, the diffuser control module 506 may turn an air source 118 and/or a diffuser element 202 (e.g., an ultrasonic plate, a nebulizer, a fan, a blower, a pump, or the like) on or off; may adjust a temperature of a heating element of the air source 118 and/or the diffuser chamber 104 (e.g., an amount of electrical power provided to a heating element or other diffuser element, a duty cycle for a heating element or diffuser element 202, or the like); or may otherwise adjust production of a diffuser stream 108.

The diffuser control module 506, in certain embodiments, may control operations of the diffuser 102 (e.g., a diffuser element 202) based on user input or other data from the communications module 504. In a further embodiment, the diffuser control module 506 may operate in cooperation with the interactive element module 502, to provide one or more effects or interactions involving the diffuser stream 108 (e.g., turning the diffuser stream 108 on or off, adjusting an intensity of the diffuser stream 108, or the like). The diffuser control module 506, in one embodiment, may control the diffuser stream 108 based on input to a user interface of the communications module 504, to allow a user to turn the diffuser 102 and/or a cover 106 on and off (e.g., start and stop the diffuser stream 108), to adjust a timing and/or intensity of the diffuser stream 108 (e.g., an intermittent or periodic timer, a shutoff timer, or the like), or to trigger another action.

The calibration module 508, in one embodiment, is configured to calibrate or adjust one or more settings of a diffuser element 202, such as an ultrasonic plate 202 or the like. The calibration module 508 may read information from a diffuser element 202, such as a model number or other identifier, an age, a current frequency, a tolerance level, and/or other information; may test a diffuser element 202 (e.g., operate the diffuser element 202 at a range of different frequencies and measure the results); or the like. Based on either information read from a diffuser element 202 and/or testing a diffuser element 202, the calibration module 508 may adjust or set one or more settings of the diffuser element 202, such as a frequency of an ultrasonic plate 202, an air speed and/or air pressure of a nebulizer 202 or air source 118, or another setting.

The calibration module 508 may store one or more settings in a table or other data structure in non-volatile storage. For example, the calibration module 508 may store a lookup table comprising model numbers for different diffuser elements 202, with corresponding settings (e.g., ultrasonic plate frequencies) for different model numbers, or the like. The calibration module 508 may calibrate and/or adjust one or more settings of a diffuser element 202 in response to one or more triggers, such as user input to the user interface 120 (e.g., a predefined sequence of one or more button presses, a user pressing a calibration button, or the like), user input received by the communications module 504, or the like.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A system comprising: a diffuser comprising, a diffuser element, disposed in a bottom of a diffuser chamber, that disperses a liquid into air within the diffuser chamber of the diffuser; and a lid comprising an annular channel adjacent to an outer edge of the lid, the annular channel opening downward toward the diffuser chamber, the lid being shaped to at least partially enclose an upper opening of the diffuser chamber, the lid comprising an external opening, protruding through the lid, shaped to form a vertical diffuser stream with pressure from a forced air source; wherein the lid comprises a splash guard, the splash guard comprises a dome shape and is adapted to slow the liquid from spilling out of the diffuser chamber when the diffuser is tipped or overturned during use; and a cover removably couplable to the diffuser over the diffuser lid such that the dispersed liquid passes through one or more openings in the cover, the cover comprising one or more decorative features having a different external shape than the diffuser.

2. The system of claim 1, further comprising a controller configured to control one or more operations of the diffuser.

3. The system of claim 2, wherein the cover further comprises an electrical interface with the diffuser, and the one or more decorative features comprise an interactive element in electrical communication with the diffuser through the electrical interface.

4. The system of claim 3, wherein the cover comprises the controller and the controller is in communication with the diffuser through the electrical interface to control the one or more operations of the diffuser.

5. The system of claim 3, wherein the diffuser comprises the controller and the controller is in communication with the interactive element through the electrical interface to control the interactive element.

6. The system of claim 3, wherein the interactive element comprises one or more of a light, a speaker, and a mechanical actuator of the cover.

7. The system of claim 3, wherein the interactive element comprises one or more valves that selectively direct the dispersed liquid through different openings of the one or more openings of the cover.

8. The system of claim 2, wherein the diffuser element comprises an ultrasonic plate and the controller is configured to calibrate the diffuser element by reading information from the diffuser element and adjusting a frequency of the ultrasonic plate.

9. The system of claim 1, wherein the cover comprises one of a plurality of compatible covers, each of the compatible covers of the plurality of compatible covers comprising one or more electrical interfaces, dispersed liquid interfaces, and an interactive element different from an interactive element of at least one other compatible cover of the plurality of compatible covers.

10. The system of claim 1, further comprising a coupling element allowing a user to release the cover from the diffuser.

11. The system of claim 10, wherein the coupling element comprises a spring loaded latch allowing the user to release the cover from the diffuser by hand, without using a tool.

12. The system of claim 1, wherein the diffuser continues to provide the dispersed liquid in response to the cover being removed.

* * * * *